(12) United States Patent
Seward

(10) Patent No.: US 7,141,041 B2
(45) Date of Patent: Nov. 28, 2006

(54) CATHETERS HAVING LATERALLY DEPLOYABLE NEEDLES

(75) Inventor: Kirk Patrick Seward, Dublin, CA (US)

(73) Assignee: Mercator Medsystems, Inc., San Learndro, CA (US)

( * ) Notice: Subject to any disclaimer, the term of this patent is extended or adjusted under 35 U.S.C. 154(b) by 616 days.

(21) Appl. No.: 10/393,700

(22) Filed: Mar. 19, 2003

(65) Prior Publication Data
US 2004/0186435 A1 Sep. 23, 2004

(51) Int. Cl.
*A61M 5/178* (2006.01)
(52) U.S. Cl. .................................. 604/164.12
(58) Field of Classification Search ........... 604/164.12, 604/19–22, 27, 48, 164.01, 164.09, 164.11
See application file for complete search history.

(56) References Cited

U.S. PATENT DOCUMENTS

| 4,578,061 | A | | 3/1986 | Lemelson | |
|---|---|---|---|---|---|
| 5,354,279 | A | * | 10/1994 | Hofling | 604/164.12 |
| 5,419,777 | A | * | 5/1995 | Hofling | 604/264 |
| 5,538,504 | A | | 7/1996 | Linden et al. | |
| 5,542,915 | A | * | 8/1996 | Edwards et al. | 604/22 |
| 6,004,295 | A | | 12/1999 | Langer et al. | |
| 6,283,947 | B1 | | 9/2001 | Mirzaee | |
| 6,283,951 | B1 | | 9/2001 | Flaherty et al. | |
| 6,302,870 | B1 | * | 10/2001 | Jacobsen et al. | 604/272 |
| 6,302,875 | B1 | * | 10/2001 | Makower et al. | 604/528 |
| 6,319,230 | B1 | * | 11/2001 | Palasis et al. | 604/164.01 |
| 6,425,887 | B1 | * | 7/2002 | McGuckin et al. | 604/272 |
| 6,730,061 | B1 | * | 5/2004 | Cuschieri et al. | 604/158 |
| 6,905,480 | B1 | * | 6/2005 | McGuckin et al. | 604/164.01 |
| 6,997,903 | B1 | * | 2/2006 | Wijay et al. | 604/117 |
| 2002/0123740 | A1 | * | 9/2002 | Flaherty et al. | 604/890.1 |

* cited by examiner

*Primary Examiner*—Sharon Kennedy
(74) *Attorney, Agent, or Firm*—Townsend and Townsend abd Crew LLP

(57) ABSTRACT

A needle injection catheter comprises a catheter body having an axially disposed needle near its distal end. The needle passes through a deflection path formed in a distal nose of the catheter. A deflection path typically comprises a 90° turn so that the axially disposed needle can be deflected laterally for advancement into surrounding tissue. Usually, a hydraulic or other driver will be provided in the distal end of the catheter in order to advance the needle and cause deflection.

6 Claims, 3 Drawing Sheets

CATHETERS HAVING LATERALLY DEPLOYABLE NEEDLES

BACKGROUND OF THE INVENTION

1. Field of the Invention

The present invention relates generally to medical methods and devices. More particularly, the present invention relates to medical methods and kits for injecting pharmaceutical agents into tissue surrounding blood vessels and other body lumens.

Coronary artery disease is the leading cause of death and morbidity in the United States and other western societies. In particular, atherosclerosis in the coronary arteries can cause myocardial infarction, commonly referred to as a heart attack, which can be immediately fatal or, even if survived, can cause damage to the heart which can incapacitate the patient. Other coronary diseases which cause death and incapacitation include congestive heart failure, vulnerable or unstable plaque, and cardiac arrhythmias. In addition to coronary artery disease, diseases of the peripheral vasculature can also be fatal or incapacitating. Vascular occlusions, blood clots and thrombus may occlude peripheral blood flow, leading to tissue and organ necrosis. Deep vein thrombosis in the legs can, in the worst cases, require amputation. Clots in the carotid artery can embolize and travel to the brain, potentially causing ischemic stroke.

While coronary artery bypass surgery is an effective treatment for stenosed arteries resulting from atherosclerosis and other causes, it is a highly invasive procedure which is also expensive and which requires substantial hospital and recovery time. Percutaneous transluminal coronary angioplasty (PTCA), commonly referred to as balloon angioplasty, is less invasive, less traumatic, and significantly less expensive than bypass surgery. Until recently, however, balloon angioplasty has not been considered to be as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in reducing subsequent restenosis resulting from hyperplasia.

Despite such improvement, patients who have undergone angioplasty procedures with subsequent stenting still suffer from a high incidence of restenosis resulting from hyperplasia. Very recently, however, experimental trials have demonstrated that the implanting of stents which have been coated with anti-proliferative drugs can significantly reduce the occurrence of hyperplasia, promising to make combined angioplasty and stenting a viable alternative to bypass surgery.

As an alternative to stent-based luminal drug delivery, the direct delivery of drug into vascular and other luminal walls has been proposed. For some time, the use of intravascular catheters having porous balloons, spaced-apart isolation balloons, expandable sleeves, and the like, have been used for releasing drugs into the inner surface of the endothelial wall of blood vessels.

Of particular interest to the present invention, catheters carrying microneedles capable of delivering therapeutic and other agents deep into the adventitial layer surrounding blood vessel lumens have been described in co-pending application Ser. No. 09/961,080, filed on Sep. 20, 2001, and Ser. No. 09/961,079, also filed on Sep. 20, 2001, both applications having common inventorship with but different assignment than the present application, the full disclosures of which are incorporated herein by reference.

The designs described in the copending applications have numerous advantages. The microneedles are delivered in a direction which is substantially perpendicular to the axis of the catheter, thus maximizing the depth of needle penetration into the wall and reducing trauma and injury. Moreover, by locating the needles on the exterior of an expanding involuted surface, the needles can be injected into tissue fully up to their point of attachment to the catheter, further maximizing the needle penetration depth which may be achieved. In some instances, however, it may be desirable to employ even longer needles than may be deployed using the catheter designs disclosed in these two copending applications.

For these reasons, it would be desirable to provide additional and improved devices and methods for the intraluminal delivery of pharmaceutical agents for the treatment of a variety of diseases. In particular, it would be desirable to provide improved needle injection catheters and methods for their use which are able to achieve a wide range of tissue injection depths, from very shallow to very deep including depths greater than the available width of the needle injection catheter being used. It would be further desirable to provide such devices and methods where the needle may be injected into tissue using a driver or other motive force located very close to the point of tissue injection to maximize the penetration force achieved. In particular, it would be desirable to avoid the need to push at the proximal end of the needle which is being injected through a catheter in order to advance the distal end into tissue. At least some of these objectives will be met by the inventions described hereinbelow.

2. Description of the Background Art

U.S. patent application Ser. Nos. 09/961,079 and 09/961,080, both filed on Sep. 20, 2001, and both having common inventorship with but different assignment than the present application, describe microneedle catheters. U.S. Pat. No. 4,578,061, describes needle injection catheters having deflectable, axially advanceable needles. U.S. Pat. No. 5,538,504, describes a needle injection catheter having a transversely oriented needle that is laterally advanced by a balloon driver. Also of interest are U.S. Pat. Nos. 6,319,230; 6,283,951; 6,283,947; 6,004,295; 5,419,777; and 5,354,279.

BRIEF SUMMARY OF THE INVENTION

Apparatus and methods according to the present invention provide for the luminal injection of pharmaceutical agents to preselected tissue depths. By deploying a deflectable needle which is oriented axially within the body lumen prior to deployment, the needle can be deflected (preferably at a 90° angle) and advanced into tissue to virtually any desired depth. By further providing a driver or other needle advancement mechanism within the body lumen near the point of deflection, efficient power transmission to the needle can be provided so that the needle injection force can be maximized. The apparatus and methods of the present invention may be used for delivering virtually any drug or other pharmaceutical agent into the tissue surrounding any natural or created body lumen and are particularly suitable for delivering the pharmaceutical agents into a perivascular region surrounding a coronary artery or other blood vessel. The perivascular region is defined as the region beyond external elastic lamina of an artery or beyond the tunica media of a vein. Usually, injection will be made directly into the vasa vasorum region of the adventitia, and it has been found that the pharmaceutical agent disperses through the adventitia circumferentially, longitudinally, and transmurally from injection site. Such distribution can provide for delivery of therapeutically effective concentrations of many drugs which would be difficult to administer in other ways.

In a first aspect of the present invention, a needle injection catheter comprises a catheter body having a distal end and a proximal end. A deflectable needle is reciprocatably mounted in a deflection path disposed within the distal end of the catheter body, and a driver is mounted in the distal end of the catheter body and coupled to axially advance the needle so that a distal end of the needle is laterally deflected by passage through the deflection path. Usually, the driver comprises a hydraulic motor. Typically, the hydraulic motor comprises a piston mechanically coupled to the needle, where the piston receives hydraulic fluid from a lumen in the catheter body. By providing pressurized hydraulic fluid through the lumen, the piston of the driver can be advanced to move the needle distally. In a particularly preferred embodiment, the hydraulic motor further includes an axially expandable hydraulic fluid receiver, usually a bellows, attached between the hydraulic fluid lumen and the piston. An interior of the bellows or other receiver receives and contains the pressurized hydraulic fluid which drives the piston. Use of the bellows reduces the risk that the pressurized hydraulic fluid will escape from the catheter during use. The needle may be retracted by withdrawing the hydraulic fluid from the bellows, optionally in combination with a return spring and/or pulling of the axial portion of the needle in a proximal direction.

Usually, the deflection path consists of a passage having an axially oriented inlet region, a curved transition region, and a straight exit region. In the specifically preferred embodiment, the straight exit region is disposed at about a 90° angle relative to the axially oriented inlet region. In this way, the needle can be advanced perpendicularly or normally into the luminal tissue surrounding the blood vessel or other body lumen.

In a second aspect of the present invention, a method for intraluminal injection of a pharmaceutical agent comprises positioning a deflectable needle in body lumen. A driver is engaged to axially advance the needle through a deflection path, typically a 90° deflection path, so that a distal end of the needle is deflected and advanced laterally into the surrounding luminal tissue. The pharmaceutical agent, typically a therapeutic or diagnostic substance, is then injected through the needle into the luminal tissue. Engaging the needle is typically performed with a driver where a pressurized hydraulic fluid is delivered to a piston in the driver which is mechanically coupled to the needle. The pressurized hydraulic fluid axially advances the piston to push the needle through the deflection path and thus into the luminal tissue as described above.

DETAILED DESCRIPTION OF THE INVENTION

Figure 1:
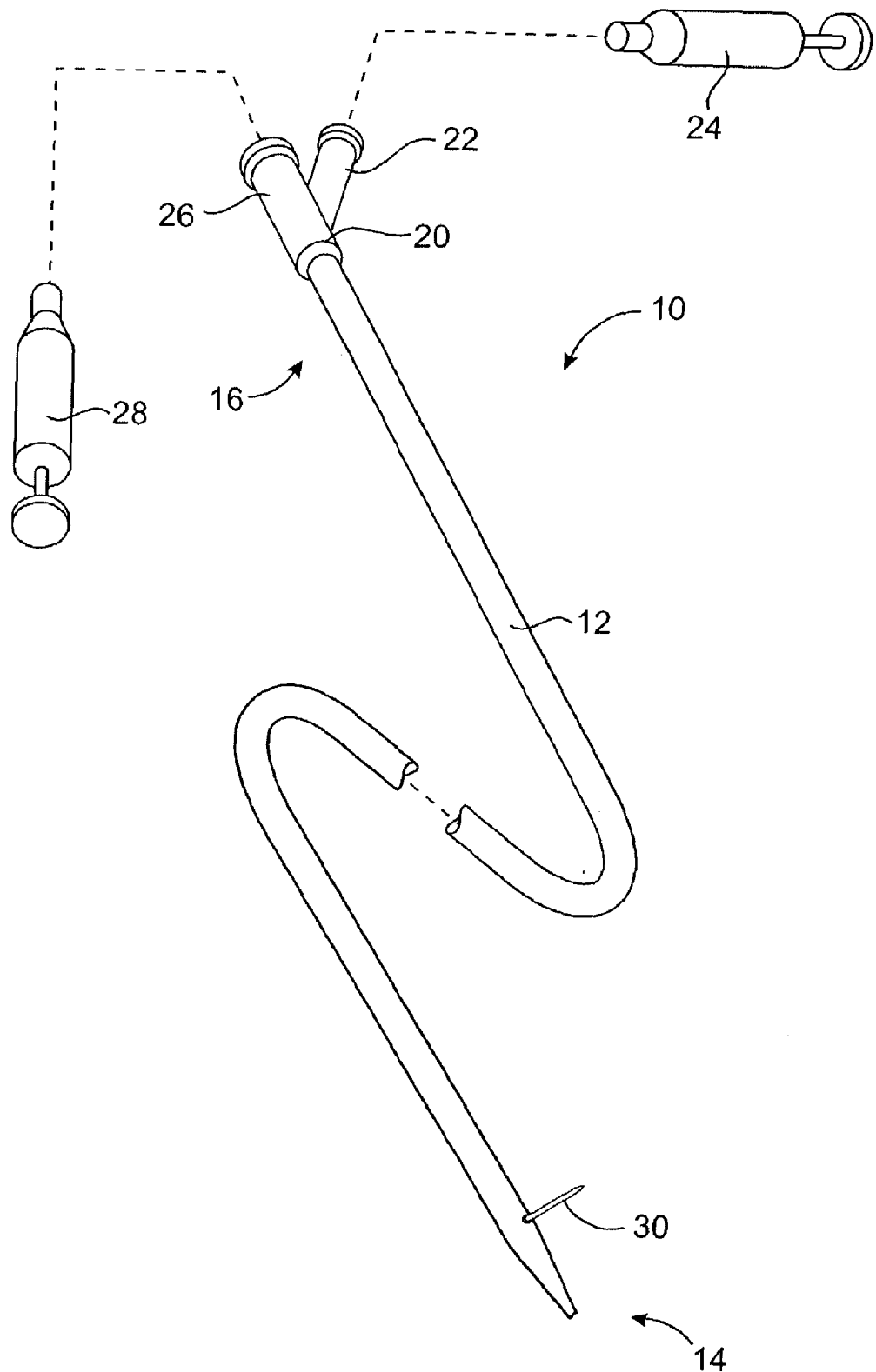
FIG. 1 is a perspective view of a needle injection catheter constructed in accordance with the principles of the present invention.

The apparatus and methods of the present invention may be used to deliver a wide variety of pharmaceutical agents into luminal tissues surrounding blood vessels and other body lumens. Exemplary pharmaceutical agents intended to treat vascular tissues surrounding coronary arteries and other blood vessels include antineoplastic agents, antiproliferative agents, cytostatic agents, immunosuppressive agents, anti-inflammatory agents, macrolide antibiotics, antibiotics, antifungals, antivirals, antibodies, lipid lowering treatments, calcium channel blockers, ACE inhibitors, gene therapy agents, anti-sense drugs, double stranded short interfering RNA molecules, metalloproteinase inhibitors, growth factor inhibitors, cell cycle inhibitors, angiogenesis drugs, anti-angiogenesis drugs, and/or radiopaque contrast media for visualization of the injection under guided X-ray fluoroscopy. Each of these therapeutic agents has shown promise in the treatment of cardiovascular disease, restenosis, congestive heart failure, and/or vulnerable plaque lesions. Particular agents are set forth in Table I.

TABLE I

1. Antiproliferative agents, immunosuppressive agents, cytostatic, and anti-inflammatory agents, including but not limited to sulindac, tranilast, ABT-578, AVI-4126, sirolimus, tacrolimus, everolimus, cortisone, dexamethosone, cyclosporine, cytochalisin D, valsartin, methyl prednisolone, thioglitazones, acetyl salicylic acid, sarpognelate, and nitric oxide releasing agents, which interfere with the pathological proliverative response after coronary antioplasty to prevent intimal hyperplasia, smooth muscle cell activation and migration, and neointimal thickening.
2. Antineoplastic agents, including but not limited to paclitaxel, actinomycin D, and latrunculin A, which interfere with the pathological proliferative response after coronary angioplasty to prevent intimal hyperplasia, smooth muscle activation and migration and neointimal thickening.
3. Macrolide antibiotics, including but not limited to sirolimus, tacrolimus, everolimus, azinthromycin, clarithromycin, and erythromycin, which inhibit or kill microorganiss that may contribute to the inflammatory process that triggers or exacerbates restenosis and vulnerable plaque. In addition many macrolide antibiotics, including but not limited to sirolimus and tacrolimus, have immunosuppressive effects that can prevent intimal hyperplasia, neointimal proliferation, and plaque rupture. Other antibiotics, including but not limited to sirolumus, tacrolimus, everolimus, azithromycin, clarithromycin, doxycycline, and erothromycin, inhibit or kill microorganisms that may contribute to the inflammatory process that triggers or exacerbates restenosis and vulnerable plaque.
4. Antivirals, including but not limited to acyclovir, ganciclovir, fancyclovir and valacyclovir, inhibit or kill viruses that may contribute to the inflammatory process that triggers or exacerbates restenosis and vulnerable plaque.
5. Antibodies which inhibit or kill microorganisms that may contribute to the inflammatory process that triggers or exacerbates restenosis and vulnerable plaque or to inhibit specific growth factors or cell TABLE I-continued regulators.
6. Lipid-lowering treatments, including but not limited to statins, such as trichostatin A, which modify plaques, reducing inflammation and stabilizing vulnerable plaques.
7. Gene therapy agents which achieve overexpression of genes that may ameliorate the process of vascular occlusive disease or the blockade of the expression of the genes that are critical to the pathogenesis of vascular occlusive disease.
8. Anti-sense agents, including but not limited to AVI-4126, achieve blockade of genes and mRNA, including but not limited to c-myc, c-myb, PCNA, cdc2, cdk2, or cdk9s, through the use of short chains of nucleic acids known as antisense oligodeoxynucleotides.
9. Metalloproteinase inhibitors, including but not limited to batimastat, inhibit constrictive vessel remodeling.
10. Cell cycle inhibitors and modulators and growth factor inhibitors and modulators, including but not limited to cytokine receptor inhibitors, such as interleukin 10 or propagermanium, and modulators of VEGF, IGF, and tubulin, inhibit or modulate entry of vascular smooth muscle cells into the cell cycle, cell migration, expression chemoattractants and adhesion molecules, extracellular matrix formation, and other factors that trigger neointimal hyperplasia.
11. Angiogenesis genes or agents which increase microvasculature of the pericardium, vaso vasorum, and adventitia to increase blood flow.
12. Anti-angiogenesis genes or agents inhibit factors that are associated with microvascularization of atherosclerotic plaque and which directly or indirectly also induce smooth muscle cell proliferation.
13. Antithrombotics including but not limited to IIb/IIIa inhibitors, Abciximab, heparin, clopidigrel, and warfarin.

Referring now to FIG. 1, a needle injection catheter 10 constructed in accordance with the principles of the present invention comprises a catheter body 12 having a distal end 14 and a proximal 16. Usually, a guide wire lumen 13 will be provided in a distal nose 52 of the catheter, although over-the-wire and embodiments which do not require guide wire placement will also be within the scope of the present invention. A two-port hub 20 is attached to the proximal end 16 of the catheter body 12 and includes a first port 22 for delivery of a hydraulic fluid, e.g., using a syringe 24, and a second port 26 for delivering the pharmaceutical agent, e.g., using a syringe 28. A reciprocatable, deflectable needle 30 is mounted near the distal end of the catheter body 12 and is shown in its laterally advanced configuration in FIG. 1.

Figure 2:
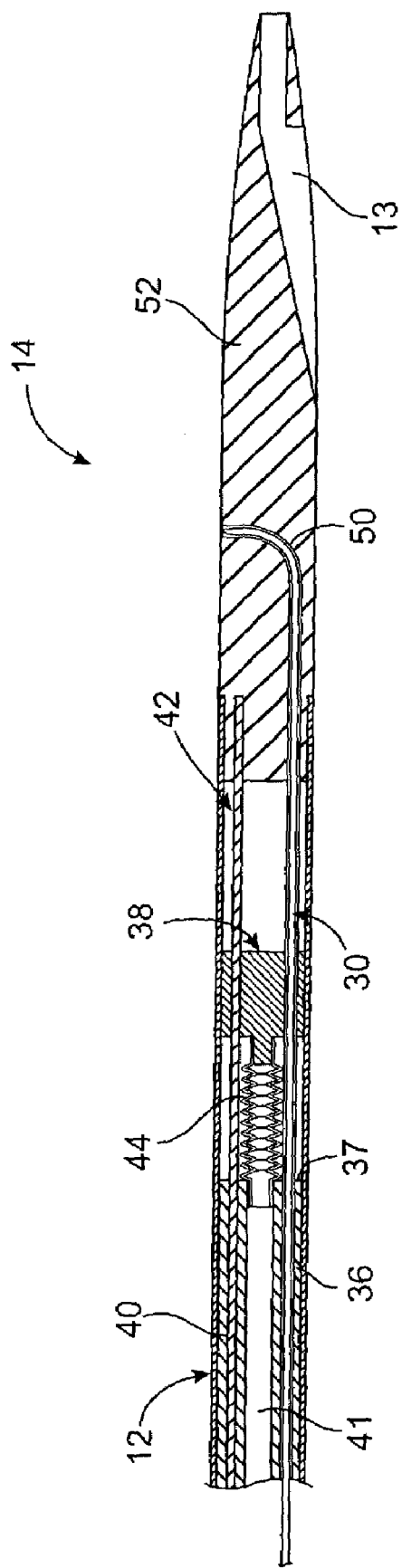
FIG. 2 is a cross-sectional view of the catheter FIG. 1 shown with the injection needle in a retracted configuration.

Referring now to FIG. 2, the distal end 14 of the catheter body 12 has a main lumen 36 which holds the needle 30, a reciprocatable piston 38, and a hydraulic fluid delivery tube 40. The piston 38 is mounted to slide over a rail 42 and is fixedly attached to the needle 30. Thus, by delivering a pressurized hydraulic fluid through a lumen 41 tube 40 into a bellows structure 44, the piston 38 may be advanced axially toward the distal tip in order to cause the needle to pass through a deflection path 50 formed in a catheter nose 52.

Figure 3:
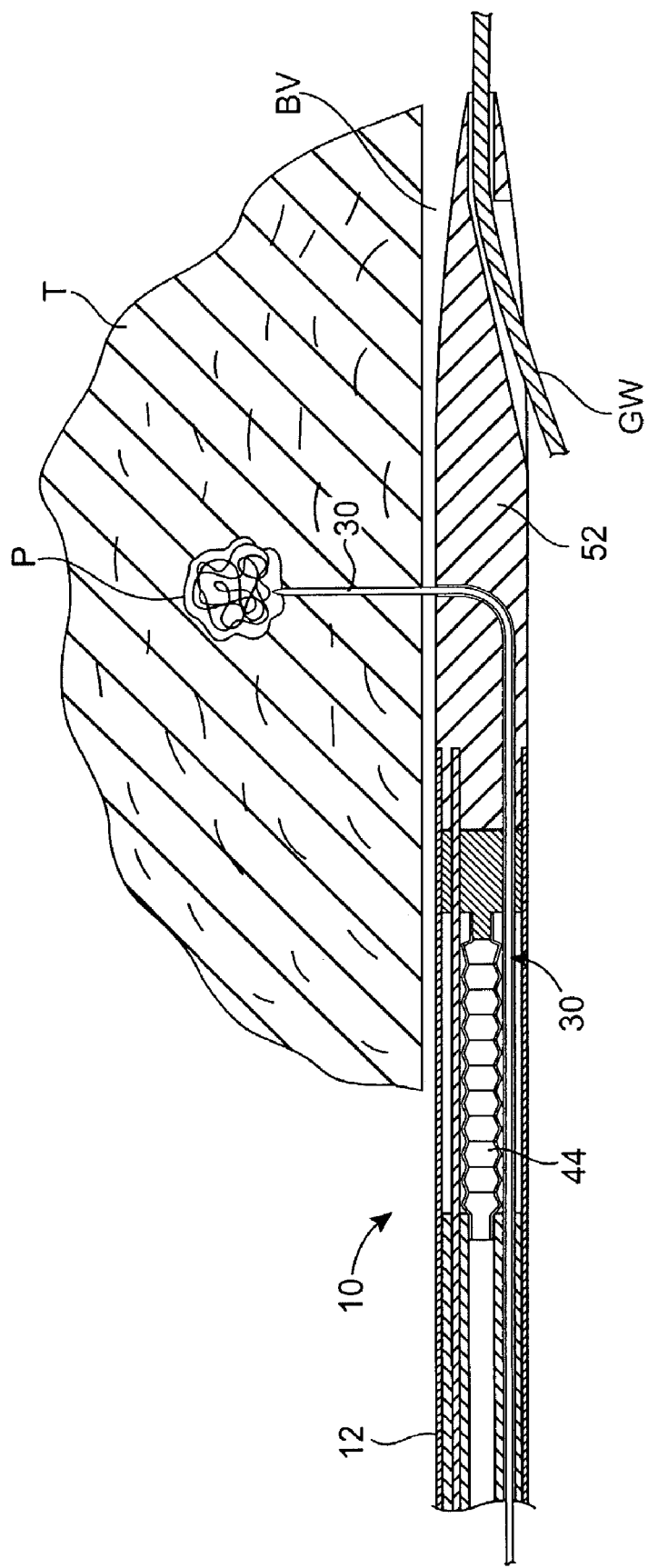
FIG. 3 is a cross-sectional view similar to FIG. 2, shown with the injection needle laterally advanced into luminal tissue for the delivery of a pharmaceutical agent.

As can be seen in FIG. 3, the catheter 10 maybe positioned in a body lumen, typically a blood vessel BV, over a guide wire GW in a conventional manner. Distal advancement of the piston 38 causes the needle 30 to advance into luminal tissue T adjacent to the catheter when it is present a target body lumen. The pharmaceutical agent may then be introduced through the port 26 using syringe 28 in order to introduce a plume P of agent in the tissue, as illustrated in FIG. 3.

The needle 30 may extend the entire length of the catheter body 12 or, more usually, will extend only partially in a pharmaceutical agent delivery lumen 37 in the tube 40. A proximal end of the needle can form a sliding seal with the lumen 37 to permit pressurized delivery of the agent through the needle.

The needle will be composed of an elastic material, typically an elastic or super elastic metal, typically being nitinol or other super elastic metal. Alternatively, the needle could be formed from a non-elastically deformable or malleable metal which is shaped as it passes through a deflection path. The use of non-elastically deformable metals, however, is less preferred since such metals will generally not retain their straightened configuration after they pass through the deflection path.

In another preferred aspect of the present invention, the bellows structure may be made by depositing by parylene or another conformal polymer layer onto a mandrel and then dissolving the mandrel from within the polymer shell structure. Alternatively, the bellows could be made from an elastomeric material to form a balloon structure. In a still further alternative, a spring structure can be utilized in, on, or over the bellows in order to drive the bellows to a closed position in the absence of pressurized hydraulic fluid therein.

After the pharmaceutical agent is delivered through the needle 30, as shown in FIG. 3, the needle is retracted and the catheter either repositioned for further agent delivery or withdrawn. In some embodiments, the needle will be retracted simply by aspirating the hydraulic fluid from the bellows 44. In other embodiments, needle retraction may be assisted by a return spring, e.g., locked between a distal face of the piston 38 and a proximal wall of the distal tip 52 (not shown) and/or by a pull wire attached to the piston and running through lumen 41.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for the intraluminal injection, said method comprising:

positioning a catheter having a deflectable needle at a distal end thereof in a body lumen, engaging a hydraulic driver disposed in the distal end of the catheter to axially advance the needle through a 90° deflection path, wherein the distal end of the needle is deflected and advanced laterally from the lumen, through luminal tissue; and injecting a therapeutic or diagnostic substance through the needle into the luminal tissue.

2. A method as in claim 1, wherein engaging a driver comprises delivering a pressurized hydraulic fluid to a piston mechanically coupled to the needle, wherein the piston is disposed in the body lumen and fluid axially advances the piston to push the needle through the deflection path.

3. A needle injection catheter comprising:
a catheter body adapted to be advanced through a body lumen and having a distal end and a proximal end;
a deflectable needle reciprocatably mounted in a deflection path disposed in the distal end of the catheter body;
a driver mounted in the distal end of the catheter body coupled to axially advance the needle so that a distal end of the needle is laterally deflected by the deflection path, wherein the driver comprises a piston mechanically coupled to the needle, wherein the piston receives hydraulic fluid from a lumen in the catheter body, wherein pressurized hydraulic fluid drives the piston and coupled needle distally.

4. A needle injection catheter as in claim 3, wherein the driver includes a bellows attached between the hydraulic fluid lumen and the piston, such that an interior of the bellows receives and contains the pressurized hydraulic fluid which drives the piston.

5. A needle injection catheter as in claim 3, wherein the deflection path consists of a passage having an axially oriented inlet region, a curved transition region, and a straight exit region.

6. A needle injection catheter as in claim 5, wherein the straight exit region is disposed at about 90° relative to the axially oriented inlet region.

* * * * *